(12) United States Patent
Hazuda et al.

(10) Patent No.: US 10,537,589 B2
(45) Date of Patent: Jan. 21, 2020

(54) METHODS FOR THE TREATMENT AND PROPHYLAXIS OF HIV AND AIDS

(71) Applicant: Merck Sharp & Dohme Corp., Rahway, NJ (US)

(72) Inventors: Daria Hazuda, Doylestown, PA (US); Michael D. Miller, Chalfont, PA (US); Jay A. Grobler, North Wales, PA (US); Deborah Anne Nicoll-Griffith, St-Basile-le-Grand (CA)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 15/430,016

(22) Filed: Feb. 10, 2017

(65) Prior Publication Data
US 2018/0055867 A1    Mar. 1, 2018

Related U.S. Application Data

(60) Provisional application No. 62/297,657, filed on Feb. 19, 2016, provisional application No. 62/294,576, filed on Feb. 12, 2016.

(51) Int. Cl.
*A61K 31/7076*    (2006.01)
*C07H 19/173*    (2006.01)
*A61K 9/20*    (2006.01)

(52) U.S. Cl.
CPC ............ *A61K 31/7076* (2013.01); *A61K 9/20* (2013.01); *C07H 19/173* (2013.01)

(58) Field of Classification Search
None
See application file for complete search history.

(56) References Cited

U.S. PATENT DOCUMENTS 7,339,053 B2    3/2008    Kohgo et al.

FOREIGN PATENT DOCUMENTS

| WO | WO2012/099630 | * | 7/2012 | ............ A61K 31/70 |
| WO | 2015148746 A1 | | 10/2015 | |
| WO | 2017053216 A2 | | 3/2017 | |

OTHER PUBLICATIONS

Ojewole et al., "Exploring the use of novel drug delivery systems for antiretroviral drugs" European Journal of Pharmaceutics and Biopharmaceutics vol. 70 pp. 697-710 (Year: 2008).*
Baert et al., "Development of an implantable infusion pump for sustained anti-HIV drug administration" International Journal of Pharmaceutics vol. 355 pp. 38-44 (Year: 2008).*
Conley et al., "Clinical spectrum of the osmotic-controlled release oral delivery system (OROS*), an advanced oral delivery form" Current Medical Research and Opinion vol. 22 No. 10 pp. 1879-1892 (Year: 2006).*
Clinical Trials.gov, Aug. 13, 2014, https://www.clinicaltrials.gov/ct2/show/study/NCT02217904?term=MK-8591&rank=1.
Cohen, C.J., et al, "Pilot Stuf of a Novel Short-Cycle Antiretroviral Treatment Interruption Strategy: 48-Week Results of The Five-Days-On, Two-Days-Off (FOTO) Study", HIV Clinical Trials, 2007, pp. 19-23, vol. 8, No. 1.
Hattori, S., et al, "Potent Activity of a Nucleoside Reverse Transcriptase Inhibitor", Antimicrobial Agents and Chemotherapy, 2009, pp. 3887-3893, vol. 53.
Kawamoto, A., et al, "2'-Deoxy-4'-C-Ethynyl-2-Halo-Adenosines Active Against Drug-Resistant Human Immunodeficiency Virus 1 Variants", International Journal of Biochemistry Cell Biology, 2008, pp. 2410-2420, vol. 40, No. 11.
Michailidis, E., et al, "4'-Ethynyl-2-Fluoro-2'-Deoxyadenosine (EFdA) inhibits HIV-1 Reverse Transcriptase With Multiple Mechanisms", Journal of Biological Chemistry, 2014, pp. 24533-24548, vol. 289, No. 35.
Michailidis, E., et al, "Mechanism of Inhibition of HIV-1 Transcriptase by 4'-Ethynyl-2-Fluoro-2'-Deoxyadenosine Triphosphate, A Translocation-Defective reverse Transcriptase Ihibitor", Journal of Biological Chemistry, 2009, pp. 35681-35691, vol. 284, No. 51.
Ohrui, H., et al, "2-Deoxy-4-C-Ethynyl-2-Fluoroaderiosine: A Nucleoside", Nucleosides, Nucleotides & Nucleic Acids, 2007, pp. 1543-1546, vol. 26.
Stoddart, C.A., et al, "Oral Administration of the Nucleoside EFdA (4'-Ethynyl-2-Fluoro-2'-Deoxyadenosine) Provides Rapid Suppression of HIV Virernia in Humanized Mice and Favorable Pharmacokinetic Properties in Mice and the Rhesus Macaque", Antimicrobial Agents and Chemotherapy, 2015, pp. 4190-4198, vol. 59, No. 7.
Murphey-Corb, Michael., et al, "Response of Simian Immunodeficiency Virus to the Novel Nucleoside Reverse Transcriptase Inhibitor 4'-Ethynyl-2-Fluoro-2-Deoxyadenosine In Vitro and In Vivo", Antimicrobial Agents and Chemotherapy, 2012, pp. 4707-4712, vol. 56, No. 9.
Anderson, P.L., et al., "Pharmacological Considerations for Tenofovir and Emtricitabine to Prevent HIV Infection", J. Antimicrobial Chemotherapy, 2011, pp. 240-250, vol. 66; and doi:10.1093/jac/dkq447 Advance Access publication Nov. 30, 2010.

(Continued)

*Primary Examiner* — Eric Olson
(74) *Attorney, Agent, or Firm* — Carol S. Quagliato; John C. Todaro

(57) ABSTRACT

The present invention is directed to methods for inhibition of HIV reverse transcriptase, treatment of infection by HIV, prophylaxis of infection by HIV, and the treatment, prophylaxis and/or delay in the onset or progression of AIDS or ARC by administering a compound of structural Formula I

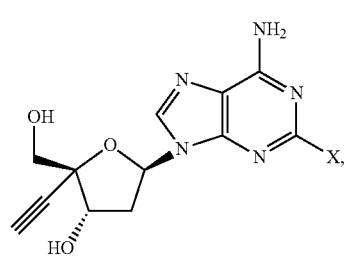

or a pharmaceutically acceptable salt or co-crystal thereof, wherein X is —F or —Cl, less frequently than once daily.

32 Claims, 3 Drawing Sheets

Specification includes a Sequence Listing.

(56) References Cited

OTHER PUBLICATIONS

Hawkins, T., et al., "Intracellular Pharmacokinetics of Tenofovir Diphosphate, Carbovir Triphosphate, and Lamivudine Triphosphate in Patients Receiving Triple-Nucleoside Regimens", Journal of Acquired Immune Deficiency Syndromes, Aug. 1 2005, pp. 406-411, vol. 39, No. 4.

Markowitz, M., et al., "Phase I/II Study of the Pharmacokinetics, Safety and Antiretroviral Activity of Tenofovir Alafenamide, A New Prodrug of the HIV Reverse Transcriptase Inhibitor Tenofovir, In HIV-Infected Adults", J. Antimicrobial Chemotherapy 2014, pp. 1362-1369, vol. 69; and doi:10.1093/jac/dkt532 Advance Access publication Feb. 6, 2014.

Lyndra Announces Publication of Feasibility Study of Oral Once-Weekly Drug Delivery System for HIV Antiretroviral Therapy in Nature Communications; Jan. 9, 2018; https://www.biospace.com/article/releases/lyndra-announces-publication-of-feasibility-study-of-oral-once-weekly-drug-delivery-system-for-hiv-antiretroviral-therapy-in-nature-cmmmunications/.

Kirtane, Ameya R., et al.,, "Development of an Oral Once-Weekly Drug Delivery System for HIV Antiretroviral Therapy", Nature Communications, 2018, pp. 1-12, vol. 9, No. 2.

\* cited by examiner

METHODS FOR THE TREATMENT AND PROPHYLAXIS OF HIV AND AIDS

RELATED APPLICATIONS

This application claims priority to U.S. Provisional Application No. 62/294576, filed Feb. 12, 2016, and to U.S. Provisional Application No. 62/297657, filed Feb. 19, 2016. Each of the aforementioned applications to which this application claims priority is herein incorporated by reference in its entirety.

REFERENCE TO SEQUENCE LISTING SUBMITTED ELECTRONICALLY

The sequence listing of the present application is submitted electronically via EFS-Web as an ASCII formatted sequence listing with a file name "24294-SEQLIST-26JULY2017.txt", having a creation date of Jul. 26, 2017 and a size of 1.65 kb. This sequence listing submitted via EFS-Web is part of the specification and is herein incorporated by reference in its entirety.

BACKGROUND OF THE INVENTION

Human immunodeficiency virus (HIV-1) infection is a serious condition which if left untreated ultimately destroys the host's immune system resulting in acquired immunodeficiency syndrome (AIDS) and premature death. Despite advances in antiretroviral therapies (ART), HIV continues to be a global epidemic and a global public health priority. An estimated 35 million people worldwide were living with HIV in 2012 (Global Report: UNAIDS report on the global AIDS epidemic 2013. UNAIDS/JC2502/1/E). In the U.S., an estimated 1.2 million people are living with HIV and about 50,000 become newly infected each year. HIV seropositive individuals are initially asymptomatic but typically develop AIDS related complex (ARC) followed by AIDS. More than 650,000 people in the U.S. have died with AIDS and more than 14,000 additional deaths are reported each year. Treatment can help people with HIV live longer, healthier lives, but currently only 30 percent of people with HIV in the U.S. are successfully keeping their virus under control. (Center for Disease Control and Prevention. Today's HIV/AIDS epidemic. July 2015).

Nucleoside reverse transcriptase inhibitors (NRTIs or NsRTIs) inhibit HIV reverse transcriptase and block HIV replication. They are one of 6 classes of HIV antiretrovirals (ARVs) used as components of potent and durable multi-drug regimens that typically combine two NRTIs (or an NRTI with an NtRTI) with a non-nucleoside reverse transcriptase inhibitor, an integrase strand transfer inhibitor, or a protease inhibitor. Combination treatment maximizes treatment response and minimizes the emergence of drug resistance.

Due to the fact that HIV replication is asynchronous, antiretroviral agents need to be continuously present in patients to effectively suppress viremia. For most classes of drugs including protease inhibitors, integrase inhibitors, and non-nucleoside reverse transcriptase inhibitors, efficacy is dictated by circulating drug concentrations and dosing is aimed at providing circulating drug concentrations throughout the dosing interval (i.e. Cmin) that exceed those required to suppress viral replication (i.e. the IC50 or IC95). In contrast, upon entering cells, NRTIs and nucleotide reverse transcriptase inhibitors (NtRTIs such as tenofovir) enter into obligate intracellular anabolic pathways for conversion to active phosphorylated forms, and it is their intracellular half-lives rather than their plasma concentrations that dictate their persistent effect. All currently approved NRTIs and NtRTIs are administered at least once-daily.

4'-Ethynyl-2-fluoro-2'-deoxyadenosine (EFdA) is a nucleoside reverse transcriptase inhibitor that blocks HIV-1 and SIV viral replication in vitro (Kawamoto, A., Kodama, E., Sarafianos S. F. et al, Int. J. Biochem. Cell Biol.; 40(11):2410-20 [2008]; Ohrui, H., Kohgo, S., Hayakawa, H. et al, *Nucleosides, Nucleotides & Nucleic Acids,* 26, 1543-1546 [2007]) and in vivo (Hattori, S., Ide, K., Nakata, H. et al. Antimicrobial. Agents and Chemotherapy, 53, 3887-3893 [2009]).

U.S. Pat. No. 7,339,053 describes EFdA (referred to in the '053 patent as 2'-deoxy-4'-C-ethynyl-2-fluoroadenosine) and 4'-ethynyl-2-chloro-2'-deoxyadenosine (referred to herein as ECdA; referred to in the '053 patent as 2-chloro-2'-deoxy-4'-C-ethynyladenosine). EFdA and ECdA have the following chemical structures:

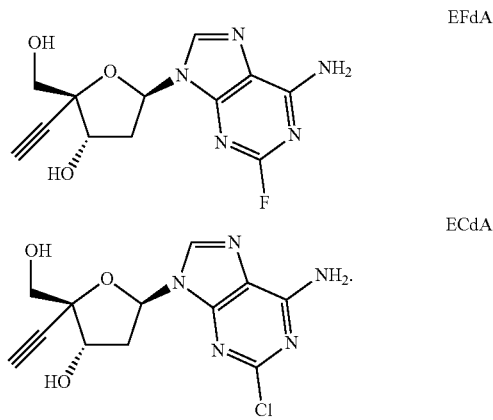

Both compounds are metabolized in cells to their active triphosphate anabolite which inhibits HIV reverse transcriptase. In contrast to NsRTIs and NtRTI's currently available for the treatment of HIV infection, which lack a 3'-OH group to block incorporation of incoming nucleotide, EFdA and ECdA retain a 3'-OH group and act as a chain terminator by preventing translocation of the primer:template in the reverse transcriptase (RT) active site and preventing binding of incoming deoxyribonucleotides triphosphates (dNTPs). In addition, the pucker of the modified ribose ring of EFdA and ECdA are believed to contribute to inhibition of reverse transcriptase by placing the 3'-OH in a vector, in which phosphotransfer from the incoming nucleotide is inefficient. (Michailidis E, et al., Mechanism of inhibition of HIV-1 reverse transcriptase by 4'-ethynyl-2-fluoro-2'-deoxyadenosine triphosphate, J Biol Chem 284: 35681-35691 [2009]; Michailidis E, et al., 4'-Ethynyl-2-fluoro-2'-deoxyadenosine (EFdA) inhibits HIV-1 reverse transcriptase with multiple mechanisms, J Biol Chem 289: 24533-24548 [2014]).

In in vitro HIV replication assays, EFdA is a potent antiretroviral and exhibits comparable antiviral activity against clinical isolates across all subtypes that have been evaluated. It is rapidly anabolized in both lymphoid derived cell lines and in peripheral blood mononuclear cells to the active triphosphate in vitro, and the intracellular half-life of EFdA Triphosphate (EFdA-TP) exceeds 72 hrs. (Stoddart, C. A., Galkina, et al., Oral Administration of the Nucleoside EFdA (4'-Ethynyl-2-Fluoro-2'-Deoxyadenosine) Provides Rapid Suppression of HIV Viremia in Humanized Mice and Favorable Pharmacokinetic Properties in Mice and the Rhesus Macaque, Antimicrob Agents Chemother, 2015 July; 59(7): 4190-4198, Published online 2015 May 4).

EFdA has been shown to have efficacy in animal models of HIV infection including humanized mouse models and an SIV infected rhesus macaque model. Pharmacokinetic studies of orally administered EFdA in mouse and rhesus monkey have demonstrated rapid absorption and robust conversion of the nucleoside to the active triphosphate in peripheral blood mononuclear cells (PBMCs). Drug concentrations achieved in both humanized mice and rhesus macaques were efficacious in suppressing viremia when administered to HIV and SIV infected animals, respectively. PBMCs that were isolated from uninfected monkeys 24 hr after drug administration were refractory to SIV infection. (Ibid.) Currently available drug treatments for HIV infection work in combination to suppress viremia, keeping the virus under control. HIV drug therapy is life-long and strict adherence to treatment regimens is critical to maintain viral suppression, reduce the risk of drug resistance, and minimize the risk of transmission. Efficacious and safe, well-tolerated drugs that are easy to take with low dosing frequency have the potential to improve a patient's adherence and long-term treatment success. For prophylaxis against HIV infection, the only currently available pre-exposure prophylaxis (PrEP) treatment approved by the U.S. Food and Drug Administration is TRUVADA® (emtricitabine/tenofovir DF) for prophylaxis against HIV infection in uninfected people.

Currently available orally administered anti-retroviral drugs are dosed once-daily. Less frequent dosing may help to alleviate both practical challenges and the cumulative psychological impact of taking daily HIV medications. Long-acting ARTs may potentially help patients return to a greater sense of normalcy and provide flexibility that could impact the way they live, work, travel, relate to others, and see themselves. Additionally, lessons from other chronic diseases requiring life-long treatment such as osteoporosis and type-2 diabetes have shown that some patients adapt to and may prefer once-weekly over once-daily dosing regimens which can result in improved medication adherence.

It would be desirable to have additional prophylactic therapy options for people at risk of HIV infection, either by administering a single active agent or a combination of active agents. Additionally, it would be desirable to have oral dosing options for HIV therapies, both for treatment and prophylaxis of HIV infection, that could be administered less frequently than dosing on a daily basis, to provide further alternatives for patients.

SUMMARY OF THE INVENTION

The present invention is directed to pre-exposure prophylaxis (PrEP) treatment using 4'-ethynyl-2-fluoro-2'-deoxyadenosine (EFdA) or 4'-ethynyl-2-chloro-2'-deoxyadenosine (ECdA), i.e., use of EFdA or ECdA, or a pharmaceutically acceptable salt or co-crystal of either active agent, for prophylaxis of HIV infection in a subject not infected with HIV who is at risk for said infection. The prophylactic treatment can be via any route or method of administration, including but not limited to administration orally, parenterally or using an implantable composition or device.

The present invention also encompasses treatment of a subject infected with HIV by parenteral administration of EFdA or ECdA, or a pharmaceutically acceptable salt or co-crystal of either active agent, employing a once-weekly or a less frequent dosing regimen. It further encompasses treatment of a subject infected with HIV by administration of EFdA or ECdA by use of an implantable composition or device which is implanted into the subject once-weekly or less frequently to deliver the active agent during the interval of time from one implant to the subsequent implant.

The present invention is further directed to oral administration of EFdA or ECdA, or a pharmaceutically acceptable salt or co-crystal of either active agent, to a subject employing oral dosing regimens for HIV therapy wherein EFdA or ECdA is administered less frequently than once daily. For example, EFdA or ECdA can be orally administered in a dosage regimen of twice-weekly dosing, once-weekly dosing, bi-weekly dosing, twice-monthly dosing, or once-monthly dosing for the inhibition of HIV reverse transcriptase, treatment of infection by HIV, prophylaxis of infection by HIV, and the prophylaxis, treatment, and/or delay in the onset or progression of AIDS and/or ARC.

DETAILED DESCRIPTION OF THE INVENTION

Figure 1:
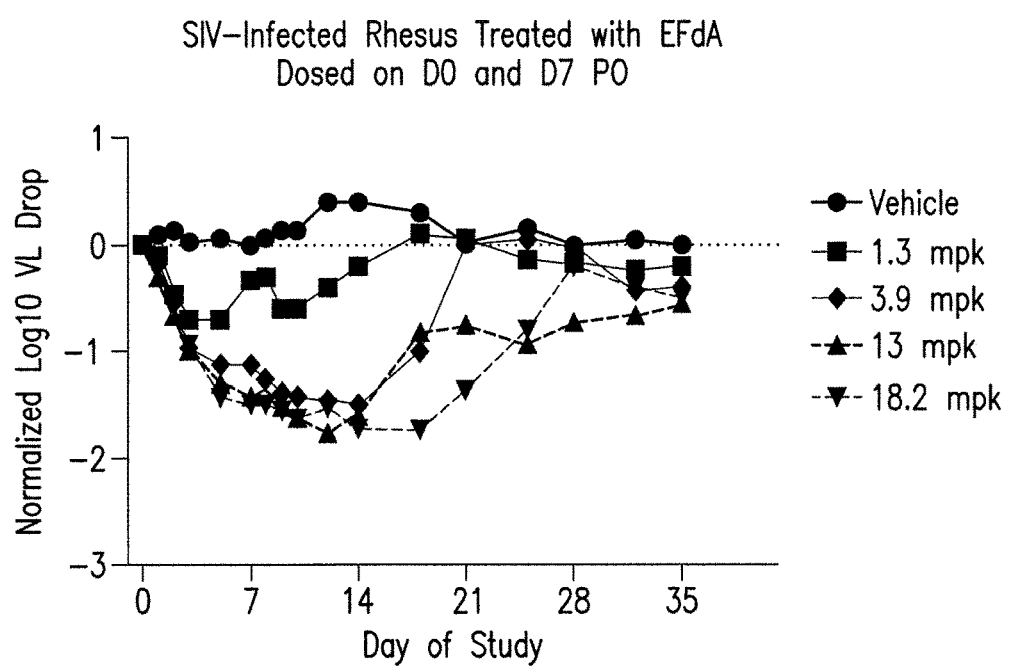
FIG. 1 is a graph of viral load changes in SIV-infected monkeys from the "Once-weekly efficacy in an SIV infected rhesus monkey model of HIV-infection" study described in Example 1.

One embodiment of the present invention, referred to herein as Embodiment A, relates to a method for the prophylaxis of HIV infection comprising administering to a subject not infected with HIV an effective amount of a compound of structural Formula I

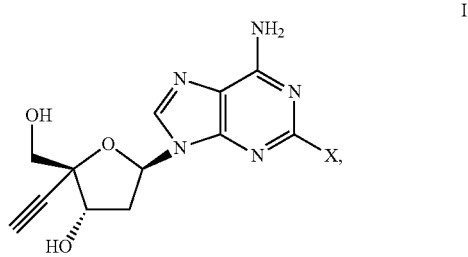

or a pharmaceutically acceptable salt or co-crystal thereof, wherein X is —F or —Cl. An effective amount of said compound may be administered to the subject once-daily, twice-weekly, once-weekly, bi-weekly, twice-monthly or once-monthly or at less frequent intervals such as once-quarterly, twice-yearly or once-yearly for prophylaxis of infection by HIV. In an aspect of this embodiment, an effective amount of said compound may be administered to the subject employing a dosing regimen wherein a compound of Formula I or a pharmaceutically acceptable salt or co-crystal thereof, is administered to the subject less frequently than once daily.

For prophylactic use against HIV infection in an uninfected subject, the compounds of Formula I, or a salt or co-crystal thereof, can be administered by any means that produces contact of the active agent with the agent's site of action. They can be administered by conventional means available for use in conjunction with pharmaceuticals, either as individual prophylactic agents or in a combination of prophylactic agents. They can be administered alone, but typically are administered with a pharmaceutical carrier selected on the basis of the chosen route of administration and standard pharmaceutical practice. The compounds of Formula I can, for example, be administered orally (e.g., via tablet or capsule), parenterally (including subcutaneous injections, intravenous, intramuscular or intrasternal injection, or other infusion techniques), or by inhalation spray, in the form of one or more unit dosage(s) of a pharmaceutical composition containing, individually or combined, an effective amount of the compound, and conventional non-toxic pharmaceutically acceptable carriers, adjuvants and vehicles for the prophylaxis of infection by HIV. The compounds of Formula I could also be administered parenterally via an implantable drug delivery composition or device adapted to provide an effective amount of the compound over an extended period of time.

Solid preparations suitable for oral administration (e.g., powders, pills, capsules and tablets) can be prepared according to techniques known in the art and can employ such solid excipients as starches, sugars, kaolin, lubricants, binders, disintegrating agents and the like. Liquid preparations suitable for oral administration (e.g., suspensions, syrups, elixirs and the like) can be prepared according to techniques known in the art and can employ any of the usual media such as water, glycols, oils, alcohols and the like. For oral administration, a solid dosage form is preferred, particularly tablets.

Parenteral compositions of the compounds of Formula I can be prepared according to techniques known in the art and typically employ sterile water as a carrier and optionally other ingredients, such as a stabilizers and/or solubility aids. Injectable solutions or injectable suspensions can be prepared according to methods known in the art, for example, wherein the carrier comprises a saline solution, a glucose solution or a solution containing a mixture of saline and glucose. Implantable compositions can also be prepared according to methods known in the art wherein, for example, the carrier comprises the active chemical ingredient with suitable excipients (e.g., polymers), or utilizing an implantable device for drug delivery.

Further description of methods suitable for use in preparing pharmaceutical compositions with the compounds of Formula I and of ingredients suitable for use in said compositions is provided in Remington's Pharmaceutical Sciences, 18$^{th}$ edition, edited by A. R. Gennaro, Mack Publishing Co., 1990 and in Remington—The Science and Practice of Pharmacy, 22nd Edition, published by Pharmaceutical Press and Philadelphia College of Pharmacy at University of the Sciences, 2012, ISBN 978 0 85711-062-6 and prior editions. Description for parenteral formulations can be found, for example, in Wright, Jeremy C. and Burgess, Diane J. (Eds.) *Long Acting Injections and Implants* (Advances in Delivery Science series), Springer New York-Dordrecht-Heidelberg-London, 2012, Print.

In an aspect of Embodiment A, a compound of Formula I could be administered for prophylaxis of infection by HIV using any suitable dosing regimen, e.g. but not limited to, administration of the compound of Formula I once daily, twice-weekly, once-weekly, bi-weekly, twice-monthly, once-monthly, once-quarterly, twice-yearly or once-yearly. In another aspect, a unit dosage of a compound of Formula I could be administered twice-weekly, once-weekly, bi-weekly, twice-monthly, once-monthly, once-quarterly, twice-yearly or once-yearly for prohylaxis of infection by HIV. In a further aspect of Embodiment A, the compound of Formula I could be administered once-weekly, bi-weekly, twice-monthly, once-monthly, once-quarterly (i.e., once every 3 months), twice-yearly (i.e., once every 6 months) or once-yearly.

In another aspect of Embodiment A wherein parenteral administration of the compound of Formula I is employed, in addition to the dosing regimens described above, less frequent dosage regimens could be used, for example but not limited to, once every 18 months or bi-annually (once every two years).

Generally, the dosage amount per administration at each time interval will increase as the time interval between each administration increases.

Preferable methods or routes of administration may also vary depending on the time interval between doses in a dosing regimen. For example, an effective amount of a compound of Formula I for prophylactic use could be administered orally at, for example but not limited to, once-daily, twice-weekly, once-weekly, bi-weekly, twice-monthly or once-monthly intervals. While oral administration of one unit dosage is preferred at each dosing interval, one or more oral unit dosage(s) may be may be adminstered at each dosing interval as needed to deliver the appropriate amount of active agent.

Alternatively, an effective amount of a compound of Formula I for prophylactic use could be administered parenterally at, for example but not limited to, once-weekly, bi-weekly, twice-monthly, once-monthly, once-quarterly, twice-yearly, once-yearly or at longer intervals, for example but not limited to, once every 18 months or bi-annually (once every two years). The longer the interval between each administration of the active agent, the greater the amount of active agent may be needed at each administration. Therefore, one or more unit dosage(s) may be adminstered at each dosing interval as needed to deliver the appropriate amount of active agent, for example, one or more injections or infusions of the compound of Formula I, or one or more implant compositions or devices.

Any dosing regimen for prophylactic use can be a continuous dosing regimen or an intermittent dosing regimen.

For prophylactic treatment, the unit dosage amount of EFdA or ECdA can range from 0.1 mg to 500 mg; or alternatively 0.1 to 400 mg or greater for longer interval dosage regimens. The dosage amount per unit dosage will vary depending on the time interval between doses in a dosing regimen.

Another embodiment of the present invention, referred to herein as Embodiment B, relates to methods for the inhibition of HIV reverse transcriptase, treatment or prophylaxis of HIV infection which includes the treatment or prophylaxis of viremia, and the treatment, prophylaxis and/or delay in the onset or progression of AIDS or ARC in a subject in need thereof, employing a dosing regimen wherein a compound of Formula I or a pharmaceutically acceptable salt or co-crystal thereof, is orally administered to the subject less frequently than once daily. Generally, the dosage amount per administration at each time interval will increase as the time interval between each administration increases.

EFdA or ECdA, optionally in the form of a salt or co-crystal, can be administered orally by any means that produces contact of the active agent with the agent's site of action. The compound can be orally administered by conventional means available for use in conjunction with pharmaceuticals, either as an individual therapeutic agent or in a combination of therapeutic agents. It can be administered alone, but typically would be administered with a pharmaceutical carrier selected for oral administration, containing an effective amount of the compound and one or more conventional non-toxic pharmaceutically acceptable carriers, adjuvants and/or vehicles. Solid preparations suitable for oral administration, for example but not limited to, tablets, capsules, powders, pills, can be prepared according to techniques known in the art and can employ such solid excipients as starches, sugars, kaolin, lubricants, binders, disintegrating agents and the like. Liquid preparations suitable for oral administration (e.g., suspensions, syrups, elixirs and the like) can be prepared according to techniques known in the art and can employ any of the usual media such as water, glycols, oils, alcohols and the like. For oral administration, a solid dosage form is preferred, particularly tablets.

In one aspect of Embodiment B is a method for the inhibition of HIV reverse transcriptase, the treatment of HIV infection which includes the treatment or prophylaxis of HIV viremia, and the treatment, prophylaxis and/or delay in the onset or progression of AIDS or ARC in an HIV infected subject which comprises orally administering to the subject an effective amount of EFdA or ECdA as a unit dosage, wherein the dosing regimen has a dosing interval range from about once every 3 days to about once every 30 days (i.e., once-monthly or once per month). Examples of the dosing regimens that can be used for oral administration of EFdA or ECdA for this method include twice-weekly dosing, once-weekly dosing, bi-weekly dosing, twice-monthly dosing, and once-monthly dosing. The selected dosing regimen would employ a dosage amount per administration suitable to provide treatment for HIV infection, AIDS or ARC, prophylaxis of AIDS or ARC, and/or delay in the onset or progression of AIDS or ARC, during the interval of time from each administration to the next.

In a further aspect of this embodiment, said dosage regimen is a continuous dosing regimen. Typically, for treatment of HIV infection or AIDS, treatment or prophylaxis of viremia, and prophylaxis against the onset or progression of AIDS or ARC in subjects infected with HIV, the selected continuous dosing regimen is maintained as long as the therapeutic effect is required or desired.

For treatment of HIV-infected patients, maintaining suppression of viremia is a desired objective. To achieve that objective, EFdA or ECdA would preferably be administered employing a continuous dosage regimen in combination with administration of one or more additional anti-HIV agents for as long as HIV viremia is effectively suppressed without viremia recrudescence.

In another aspect of Embodiment B is a method for the prophylaxis of HIV infection in a subject not infected with HIV which comprises orally administering to the subject an effective amount of EFdA or ECdA as a unit dosage, wherein the dosing regimen has a dosing interval range from about once every 3 days to about once every 30 days. Examples of the dosing regimens for prophylaxis of HIV infection that can be used for oral administration of EFdA or ECdA include twice-weekly dosing, once-weekly dosing, bi-weekly dosing, twice-monthly dosing, and once-monthly dosing. In one aspect of this embodiment, said dosage regimen is a continuous dosing regimen. In another aspect of this embodiment, said dosage regimen is an intermittent dosing regimen.

For prophylaxis against HIV-infection in an uninfected subject, EFdA or ECdA can be orally administered using either a continuous dosing regimen or an intermittent dosing regimen using one or more of the dosing regimens described herein (e.g., twice-weekly dosing, once-weekly dosing, bi-weekly dosing, twice-monthly dosing, and once-monthly dosing) as long as necessary or desired to prevent or reduce the risk for the transmission of HIV. The selected dosing regimen would employ a dosage amount per administration suitable to provide prophylactic effect during the interval of time from each administration to the next.

While oral administration of one unit dosage is preferred at each dosing interval, one or more oral unit dosage(s) may be may be adminstered at each dosing interval as needed to deliver the appropriate amount of active agent.

For intermittent dosing regimens for prophylaxis against HIV-infection in an uninfected subject, a single period of adhering to a dosage regimen (e.g., one dose in one week for a weekly dosing regimen) or consecutive repeated periods of adhering to a dosage regimen (e.g., one dose per week for 3 consecutive weeks employing a weekly dosing regimen) could be followed by a period of not dosing, followed by another period of employing a dosing regimen. An example of an intermittent dosing regimen for prophylaxis of HIV infection includes but is not limited to, administering an effective dosage amount of EFdA or ECdA once per week for 1 or 2 weeks, then not dosing for 1 or 2 months, then re-starting administering once-weekly dosing of EFdA or ECdA for 1 or 2 weeks. The overall period of time that a subject may use an intermittent dosing regimen can range, for example, from about 1 week to the remaining lifespan of the patient, wherein a dosing regimen, during the period(s) of time it is employed, is less frequent than once daily dosing as described herein.

For oral (e.g., tablets or capsules) administration, the dosage units may each contain from 0.1 mg to 500 mg; or alternatively 0.1 to 400 mg of EFdA or ECdA. The dosage amount per unit dosage will vary depending on the time interval between doses in a dosing regimen, Examples of unit dosage amounts of EFDA or a pharmaceutically acceptable salt or co-crystal thereof include but are not limited to the following.

For a twice-weekly dosing regimen: each unit dosage may be comprised of EFdA or ECdA in an amount from 0.5 mg to 25 mg, alternatively from 0.5 mg to 10 mg; or more specifically 0.5 mg, 1 mg, 2 mg, 3 mg, 4 mg or 5 mg.

For a once-weekly dosing regimen: each unit dosage may be comprised of EFdA or ECdA in an amount from 1 mg to 50 mg, alternatively from 1 mg to 20 mg; or more specifically 1 mg, 2 mg, 3 mg, 4 mg, 5 mg, 6 mg, 7 mg, 8 mg, 9 mg or 10 mg.

For a bi-weekly or twice-monthly dosing regimen: each unit dosage may be comprised of EFdA or ECdA in an amount from 2 mg to 100 mg, alternatively from 2 mg to 40 mg; or more specifically 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg or 20 mg.

For a once-monthly dosing regimen: each unit dosage may be comprised of EFdA or ECdA in an amount from 4 mg to 200 mg, alternatively from 4 mg to 80 mg; or more specifically 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg or 20 mg; 21 mg, 22 mg, 23 mg, 24 mg, 25 mg, 26 mg, 27 mg, 28 mg, 29 mg or 30 mg, 31 mg, 32 mg, 33 mg, 34 mg, 35 mg, 36 mg, 37 mg, 38 mg, 39 mg or 40 mg.

Dosage amounts for ECdA can be about 2 to 4 times higher than for EFdA.

When EFdA or ECdA is administered as a salt or a co-crystal, reference to an amount of the compound in milligrams or grams is based on the weight of the free form of EFdA or ECdA (i.e., the non-salt or non-co-crystal form) of the compound.

The minimum dosage amount of EFdA or ECdA will vary with the dosing regimen, and whether the intended use is for treatment and/or prophylaxis for subjects infected with HIV, or for prophylaxis for subjects not infected with HIV. A non-limiting example for once-weekly oral dosing for a subject infected with HIV is a unit dosage comprising about 10 mg of EFdA or ECdA for treatment and/or prophylaxis of conditions as described above. A non-limiting example for once-weekly oral dosing for prevention of HIV-infection in an uninfected subject is a unit dosage comprising about 2 mg of EFdA or ECdA.

Another embodiment of the present invention, referred to herein as Embodiment C, relates to methods for the inhibition of HIV reverse transcriptase, treatment of HIV infection which includes the treatment of viremia, and the treatment, prophylaxis and/or delay in the onset or progression of AIDS or ARC, by parenterally administering an effective amount of a compound of Formula I, or a pharmaceutically acceptable salt or co-crystal thereof, to a subject infected with HIV, employing a dosing regimen wherein the compound is parenterally administered less frequently than once daily.

The compounds of Formula I can be administered parenterally, including subcutaneous injections, intravenous, intramuscular or intrasternal injection, or other infusion techniques (one or more injections or infusions may be administered at each dosing interval as needed to deliver the appropriate amount of active agent), or by inhalation spray, in the form of a unit dosage of a pharmaceutical composition containing an effective amount of the compound and conventional non-toxic pharmaceutically acceptable carriers, adjuvants and vehicles for the treatment of a subject infected with HIV. The compounds of Formula I could also be administered parenterally via an implantable drug delivery composition or device adapted to provide an effective amount of the compound over an extended period of time. Preparation of parenteral compositions as described above for use in a subject not infected with HIV (see Embodiment A) are likewise suitable for preparation of parenteral compositions for treatment of a subject infected with HIV. A continuous dosing regimen should be used for treatment of HIV infected subjects.

In an aspect of Embodiment C, a unit dosage of an effective amount of a compound of Formula I could be administered parenterally at, for example but not limited to, once-weekly, bi-weekly, twice-monthly, once-monthly, once-quarterly, twice-yearly or once-yearly intervals or at longer intervals, for example but not limited to, once every 18 months or bi-annually (once every two years).

In a further aspect of Embodiment C, the compound could be administered parenterally at once-monthly, once-quarterly, twice-yearly or once-yearly intervals.

The longer the interval between each administration of the active agent, the greater the amount of active agent may be needed at each administration. Therefore, one or more unit dosage(s) may be administered at each dosing interval as needed to deliver the appropriate amount of active agent, for example, one or more injections or infusions or one or more implant compositions or devices comprising a compound of Formula I.

The present invention, which includes all embodiments, aspects, and descriptions recited herein, is also directed to use of EFdA or ECdA in the dosing regimens as described above with administration of one or more anti-HIV agents. An "anti-HIV agent" is any agent which is directly or indirectly effective in the inhibition of HIV, the treatment or prophylaxis of HIV infection, and/or the treatment, prophylaxis or delay in the onset or progression of AIDS or ARC. It is understood that an anti-HIV agent is effective in treating, preventing, or delaying the onset or progression of HIV infection or AIDS and/or diseases or conditions arising therefrom or associated therewith. For example, the compounds of Formula I may be effectively administered, whether at periods of pre-exposure and/or post-exposure, in combination with effective amounts of one or more other anti-HIV agents selected from HIV antiviral agents, immunomodulators, antiinfectives, or vaccines useful for treating HIV infection or AIDS.

The present invention encompasses pharmaceutical compositions comprising an effective amount of EFdA or ECdA and a pharmaceutically acceptable carrier. Said composition may comprise EFdA or ECdA as the only active ingredient or may include one or more additional active ingredients. Accordingly, the present invention further encompasses pharmaceutical compositions comprising an effective amount of EFdA or ECdA and a pharmaceutically acceptable carrier further comprising an effective amount of one or more additional anti-HIV agents selected from one or more of HIV antiviral agents, immunomodulators, and ant-infective agents. Within this embodiment, the anti-HIV agent is an antiviral selected from one or more of HIV protease inhibitors, HIV reverse transcriptase inhibitors, HIV integrase inhibitors, HIV fusion inhibitors, HIV entry inhibitors, and HIV maturation inhibitors.

Suitable HIV antivirals for use in combination with a compound of the present invention include but are not limited to, for example, those listed in Table A.

TABLE A

Antiviral Agents for Treating HIV infection or AIDS

| Name | Type |
| --- | --- |
| abacavir, ABC, Ziagen ® | nRTI |
| abacavir + lamivudine, Epzicom ® | nRTI |
| abacavir + lamivudine + zidovudine, Trizivir ® | nRTI |
| amprenavir, Agenerase ® | PI |
| atazanavir, Reyataz ® | PI |
| AZT, zidovudine, azidothymidine, Retrovir ® | nRTI |
| capravirine | nnRTI |
| darunavir, Prezista ® | PI |
| ddC, zalcitabine, dideoxycytidine, Hivid ® | nRTI |
| ddI, didanosine, dideoxyinosine, Videx ® | nRTI |
| ddI (enteric coated), Videx EC ® | nRTI |
| delavirdine, DLV, Rescriptor ® | nnRTI |
| dolutegravir, Tivicay ® | InI |
| doravirine, MK-1439 | nnRTI |
| efavirenz, EFV, Sustiva ®, Stocrin ® | nnRTI |
| efavirenz + emtricitabine + tenofovir DF, Atripla ® | nnRTI + nRTI |
| elvitegravir | InI |
| emtricitabine, FTC, Emtriva ® | nRTI |
| emtricitabine + tenofovir DF, Truvada ® | nRTI |
| emvirine, Coactinon ® | nnRTI |
| enfuvirtide, Fuzeon ® | FI |
| enteric coated didanosine, Videx EC ® | nRTI |
| etravirine, TMC-125 | nnRTI |
| fosamprenavir calcium, Lexiva ® | PI |
| indinavir, Crixivan ® | PI |

TABLE A-continued

Antiviral Agents for Treating HIV infection or AIDS

| Name | Type |
|---|---|
| lamivudine, 3TC, Epivir ® | nRTI |
| lamivudine + zidovudine, Combivir ® | nRTI |
| lopinavir | PI |
| lopinavir + ritonavir, Kaletra ® | PI |
| maraviroc, Selzentry ® | EI |
| nelfinavir, Viracept ® | PI |
| nevirapine, NVP, Viramune ® | nnRTI |
| PPL-100 (also known as PL-462) (Ambrilia) | PI |
| raltegravir, MK-0518, Isentress ™ | InI |
| rilpivirine | nnRTI |
| ritonavir, Norvir ® | PI |
| saquinavir, Invirase ®, Fortovase ® | PI |
| stavudine, d4T, didehydrodeoxythymidine, Zerit ® | nRTI |
| tenofovir DF (DF = disoproxil fumarate), TDF, Viread ® | nRTI |
| tenofovir alafenamide fumarate, TAF | nRTI |
| tipranavir, Aptivus ® | PI |
| vicriviroc | EI |

EI = entry inhibitor;
FI = fusion inhibitor;
InI = integrase inhibitor;
PI = protease inhibitor;
nRTI = nucleoside reverse transcriptase inhibitor;
nnRTI = non-nucleoside reverse transcriptase inhibitor. Some of the drugs listed in Table A are used in a salt form; e.g., abacavir sulfate, delavirdine mesylate, indinavir sulfate, atazanavir sulfate, nelfinavir mesylate, saquinavir mesylate.

It is understood that the scope of combinations of the compounds of Formula I with anti-HIV agents is not limited to the HIV antivirals listed in Table A, but includes in principle any combination with any pharmaceutical composition useful for the treatment and/or prophylaxis of HIV and AIDS. The HIV antiviral agents and other agents will typically be employed in these combinations in their conventional dosage ranges and regimens as reported in the art, including, for example, the dosages described in the Physicians' Desk Reference, Thomson PDR, Thomson PDR, 57th edition (2003), the 58th edition (2004), or the 59th edition (2005) and the Physicians' Desk Reference (68th ed.). (2014), Montvale, N.J.: PDR Network. The dosage ranges for a compound of the present invention in these combinations can be the same as those set forth above.

The present invention also encompasses EFdA or ECdA for use in the preparation of a medicament useful for any one or more of the inhibition of HIV reverse transcriptase, the treatment of infection by HIV, the prophylaxis of infection by HIV, or the treatment, prophylaxis and/or delay in the onset or progression of AIDS or ARC in a subject in need thereof. It further encompasses the administration of EFdA or ECdA in combination with one or more additional anti-HIV agents selected from one or more of HIV antiviral agents, immunomodulators, and anti-infective agents for use in the preparation of a medicament for any one or more of the inhibition of HIV reverse transcriptase, the treatment of infection by HIV, the prophylaxis of infection by HIV, the treatment of AIDS, or the prophylaxis or delay in the onset or progression of AIDS in a subject in need thereof. Within this embodiment of the present invention, the anti-HIV agent is an antiviral selected from one or more of HIV protease inhibitors, HIV reverse transcriptase inhibitors, HIV integrase inhibitors, HIV fusion inhibitors, HIV entry inhibitors, and HIV maturation inhibitors.

An additional embodiment of the present invention includes the methods, pharmaceutical compositions, medicaments, uses and combinations set forth herein, wherein the HIV of interest is HIV-1. Thus, for example, in any of the methods, pharmaceutical compositions, medicaments, uses and combinations using the described dosage regimens set forth herein, EFdA or ECdA is employed in an amount effective against HIV-1; and when used in combination with one or more anti-HIV agent(s), each additional anti-HIV agent is an HIV-1 antiviral selected from one or more of HIV-1 protease inhibitors, HIV-1 reverse transcriptase inhibitors, HIV-1 integrase inhibitors, HIV-1 fusion inhibitors, HIV-1 entry inhibitors or HIV-1 maturation inhibitors.

EFdA and/or ECdA may also exhibit activity against HIV-2 when administered twice-weekly, once weekly or less frequently in the dosage regimens described herein. EFdA or ECdA also may exhibit activity against drug resistant forms of HIV (e.g. NRTI-associated mutant strains M184V, M184I, K65R).

The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the subject undergoing therapy. In some cases, depending on the potency of the compound or the individual response, it may be necessary to deviate upwards or downwards from the given dose. The amount and frequency of administration may be regulated according to the judgment of the attending clinician considering such factors.

In another embodiment of the present invention, in each of the methods, pharmaceutical compositions, medicaments, uses, combinations, aspects and other embodiments described and/or claimed herein, the compound of Formula I is EFdA or a pharmaceutically acceptable salt or co-crystal thereof (i.e., wherein X is —F).

In another embodiment of the present invention, in each of the methods, pharmaceutical compositions, medicaments, uses, combinations, aspects and other embodiments described and/or claimed herein, the compound of Formula I is ECdA or a pharmaceutically acceptable salt or co-crystal thereof (i.e., wherein X is —Cl).

For brevity, the phrase "or a pharmaceutically acceptable salt or co-crystal thereof" is not always recited following the term "compound of Formula I," "EFdA" or "ECdA" herein. However, reference to the use of a compound of Formula I, EFdA or ECdA in the methods, pharmaceutical compositions, medicaments, uses, combinations, aspects and other embodiments described and/or claimed herein is intended include the use of a compound of Formula I, EFdA or ECdA (where each term appears) or a pharmaceutically acceptable salt or co-crystal thereof.

The term "subject" or "patient" as used herein refers to an animal, preferably a mammal, most preferably a human, who has been or will be the object of treatment including prophylactic treatment, observation or experiment. Human subjects or patients include (1) those infected with HIV with or without AIDS who are seeking treatment for HIV infection, ARC or AIDS, and/or prophylaxis and/or delay in the onset or progression of ARC or AIDS, and (2) those not infected with HIV who are seeking or receiving prophylactic treatment to prevent or reduce the risk for transmission of HIV. In an embodiment of this invention, each of the methods, pharmaceutical compositions, medicaments, uses, combinations, aspects and other embodiments described and/or claimed herein, the subject is a human subject.

The term "effective amount" as used herein means an amount of a compound sufficient to inhibit HIV reverse transcriptase, inhibit HIV replication, exert a prophylactic effect, and/or a exert a therapeutic effect after administration. One embodiment of "effective amount" is a "therapeutically effective amount" which is an amount of a compound that is effective for inhibiting HIV reverse transcriptase, inhibiting HIV replication (either of the foregoing which may also be referred to herein as an "inhibition effective amount"), treating HIV infection, treating AIDS or ARC, and/or slowing progression of AIDS or ARC in a patient. Another embodiment of "effective amount" is a "prophylactically effective amount" which is an amount of the compound that is effective for prophylaxis of HIV infection, delaying the onset of AIDS or ARC, or prophylaxis of AIDS or ARC in a patient. It is understood that in an HIV infected subject, an effective amount could simultaneously be both a therapeutically effective amount, e.g., for treatment of HIV infection, and a prophylactically effective amount, e.g., for prevention or reduction of risk for developing AIDS or ARC or for delaying the onset or progression of AIDS or ARC.

Prophylaxis (or prevention) of infection by HIV in an uninfected subject is intended to mean preventing or reducing the likelihood of HIV infection in the subject. In a subject infected with HIV, prophylaxis (or prevention) of AIDS or ARC is intended to mean preventing or reducing the likelihood for developing AIDS or ARC in the subject.

Another embodiment of "effective amount" encompasses an amount of EFdA or ECdA that reduces viremia in HIV infected subjects or that prevents HIV infection of uninfected people that are exposed to the virus.

In the combination therapies of the present invention, an effective amount can refer to each individual agent or to the combination as a whole, wherein the amounts of all agents administered in the combination are together effective, but wherein a component agent of the combination may or may not be present individually in an effective amount with reference to what is considered effective for that component agent if it were administered alone. The term "administration" and variants thereof (e.g., "administering" a compound) with reference to the methods herein, means providing the compound to the subject in need of treatment or prophylaxis and includes both self-administration and administration to the patient by another person. When EFdA or ECdA is provided in combination with one or more other active agents (e.g., antiviral agents useful for treating or prophylaxis of HIV infection or AIDS), "administration" and its variants are each understood to include provision of EFdA or ECdA and the other agent(s) to the subject at the same time (i.e., all on the same dosing regimen schedule) or at different times if the other agent(s) cannot be dosed on the same dosage regimen schedule as EFdA or ECdA. When the agents of a combination are administered at the same time, they can be administered together in a single composition or they can be administered separately.

SIV=Simian Immunodeficiency Virus; VL=viral load; LLQ=lower limit of quantitation.

Dosing regimens of the present invention that employ dosing of EFdA or ECdA less frequently than once daily are described above. Reference to dosing "intervals" may also be recited herein to describe dosing regimens. The term "continuous dosing regimen" as used herein, means a dosing regimen that is repeated without breaks for as long as the desired therapeutic effect or prophylactic effect is required or deemed appropriate by a clinician or patient. The term "intermittent dosing regimen" as used herein means a dosing regimen to be used for one or more limited periods of time for periodic prophylaxis to prevent or reduce the risk for transmission of HIV with stoppage of the dosing regimen after one period or between periods of employing the dosing regimen.

The present invention provides dosing regimens whereby a unit dosage of the EFdA or ECdA is regularly administered according to a dosing interval selected from once-weekly dosing, twice-weekly dosing, bi-weekly dosing, twice-monthly dosing, and once-monthly dosing. The phrase "once-weekly" dosing as used herein means that a unit dosage of EFdA or ECdA is administered once per week, i.e. one time during a seven day period, preferably on the same day of each week. In the once-weekly dosing regimen, the dosage is generally administered about every seven days. A nonlimiting example of a once-weekly dosing regimen would entail the administration of a unit dosage of EFdA or ECdA every Sunday. It is preferred that the unit dosage is administered once every 7 days, but the once-weekly dosing regimen encompasses a dosing regimen in which a unit dosage is administered every 5 to 10 days as long as two consecutive doses fall within two different weekly periods.

The phrase "twice-weekly" dosing as used herein means that a unit dosage of EFdA or ECdA is administered twice per week, i.e., two times during a seven day period, on two different days each weekly period wherein the 2 days are preferably the same each week. In the twice-weekly dosing regimen, each unit dosage is generally administered about every three to four days. A nonlimiting example of a twice weekly regimen would entail the administration of a unit dosage of EFdA or ECdA every Sunday and Wednesday. It is preferred that the unit dosages are administered every 3 to 4 days, but the twice weekly dosing regimen encompasses a dosing regimen in which a unit dosage is administered every 2 to 5 days as long as two doses are administered within each weekly period.

The phrase "bi-weekly" dosing as used herein means that a unit dosage of EFdA or ECdA is administered once during a two week period, i.e. one time during a fourteen day period, preferably on the same day during each two week period. In the bi-weekly dosing regimen, each unit dosage is generally administered once every fourteen days. A nonlimiting example of a bi-weekly dosing regimen would entail the administration of a unit dosage of EFdA or ECdA every other Sunday. It is preferred that the unit dosage is administered once every 14 days, but the bi-weekly dosing regimen encompasses a dosing regimen in which a unit dosage is administered every 12 to 16 days as long as two consecutive doses fall within two different bi-weekly periods.

The phrase "twice-monthly" dosing as used herein means that a unit dosage of EFdA or ECdA is administered twice, i.e. two times, during a monthly calendar period. With the twice-monthly regimen, the doses are preferably given on the same two dates of each month. In the twice-monthly dosing regimen, each unit dosage is generally administered about every fourteen to sixteen days. A nonlimiting example of a twice-monthly dosing regimen would entail dosing on or about the first of the month and on or about the fifteenth of the month, i.e. the midway point of the month. It is preferred that the unit dosages are administered every 14 to 16 days, but the twice-monthly dosing regimen encompasses a dosing regimen in which a unit dosage is administered every 13 to 18 days as long as two doses are administered within a monthly period. The twice-monthly regimen is defined herein as being distinct from, and not encompassing, the bi-weekly dosing regimen because the two regimens have a different periodicity and result in the administration of different numbers of dosages over long periods of time. For example, over a one year period, a total of about twenty four dosages would be administered according to the twice monthly regimen (because there are twelve calendar months in a year), whereas a total of about twenty six dosages would be administered according to the bi-weekly dosing regimen (because there are about fifty-two weeks in a year).

The phrase "once-monthly" (or "once per month") dosing as used herein means that a unit dosage of EFdA or ECdA is administered once during a one month period, i.e. one time during a monthly calendar period, preferably on the same day during each one month period. In the once-monthly dosing regimen, each unit dosage is generally administered once every 28-31 days. A non-limiting example of a once-monthly dosing regimen would entail the administration of a unit dosage of EFdA or ECdA on or about the first day of every month. It is preferred that the unit dosage is administered once every 28-31 days, but the once-monthly dosing regimen encompasses a dosing regimen in which a unit dosage is administered every 27 to 33 days as long as two consecutive doses fall within two different monthly periods.

The phrase "once-quarterly" dosing as used herein means that a unit dosage of EFdA or ECdA is administered once during a 3 month period, i.e. one time during a quarterly calendar period, preferably on the same date during each quarterly period. In the once-quarterly dosing regimen, each unit dosage is generally administered once every 84-93 days. A non-limiting example of this dosing regimen would entail the administration of a unit dosage of EFdA or ECdA on or about the 1st day of the first month of each quarterly period. It is preferred that the unit dosage is administered once every 84-93 days, but the once-quarterly dosing regimen encompasses a dosing regimen in which a unit dosage is administered every 81 to 99 days as long as two consecutive doses fall within two different 3 month periods.

The phrase "twice-yearly" dosing as used herein means that a unit dosage of EFdA or ECdA is administered once during a 6 month period, i.e. one time during a 6 month calendar period, preferably on the same date during each twice-yearly period. In the twice-yearly dosing regimen, each unit dosage is generally administered once every 168-186 days. A non-limiting example of this dosing regimen would entail the administration of a unit dosage of EFdA or ECdA on or about the 1st day of the first month of each twice-yearly period. It is preferred that the unit dosage is administered once every 168-186 days, but the twice-yearly dosing regimen encompasses a dosing regimen in which a unit dosage is administered every 162-198 days as long as two consecutive doses fall within two different 6 month periods.

The phrase "once-yearly" dosing as used herein means that a unit dosage of EFdA or ECdA is administered once during a 12 month period, i.e. one time during a 12 month calendar period, preferably on the same date during each once-yearly period. In the once-yearly dosing regimen, each unit dosage is generally administered once every 336-372 days. A non-limiting example of this dosing regimen would entail the administration of a unit dosage of EFdA or ECdA on or about the 1st day of the first month of each once-yearly period. It is preferred that the unit dosage is administered once every 336-372 days, but the once-yearly dosing regimen encompasses a dosing regimen in which a unit dosage is administered every 324-396 days as long as two consecutive doses fall within two different 12 month periods.

EFdA or ECdA can be administered in the form of a pharmaceutically acceptable salt or pharmaceutically acceptable co-crystal. The term "pharmaceutically acceptable salt" and "pharmaceutically acceptable co-crystal" refers to a salt or co-crystal which is not biologically or otherwise undesirable (e.g., is neither toxic nor otherwise deleterious to the recipient thereof). Since EFdA or ECdA contains at least one basic group on the fluoroadenine base, the present invention includes the corresponding pharmaceutically acceptable salts. Since EFdA or ECdA contains at least one basic group on the adenine base, i.e. a group which can be protonated, it can be used according to the present invention in the form of its acid addition salts with inorganic or organic acids such as, for example but not limited to, salts with hydrogen chloride, hydrogen bromide, phosphoric acid, sulfuric acid, nitric acid, benzenesulfonic acid, methanesulfonic acid, p-toluenesulfonic acid, naphthalenedisulfonic acids, trifluoroacetic acid, tartaric acid, lactic acid, salicylic acid, benzoic acid, formic acid, propionic acid, pivalic acid, succinic acid, etc. EFdA or ECdA can be used according to the present invention in the form of its acid co-crystals with inorganic or organic acids as, for example but not limited to, salts benzenesulfonic acid, methanesulfonic acid, p-toluenesulfonic acid, naphthalenedisulfonic acids, trifluoroacetic acid, tartaric acid, lactic acid, salicylic acid, benzoic acid, formic acid, propionic acid, pivalic acid, succinic acid, etc. Salts and co-crystals can be obtained from EFdA or ECdA by customary methods which are known to the person skilled in the art, for example by combination with an organic or inorganic acid or base in a solvent or dispersant, or by ion exchange from other salts.

As used herein, the term "composition" is intended to encompass a product comprising the specified ingredients, as well as any product which results from combining the specified ingredients. Ingredients suitable for inclusion in a pharmaceutical composition are pharmaceutically acceptable ingredients, which means the ingredients must be compatible with each other and not deleterious to the recipient thereof.

EXAMPLE 1

Once-weekly efficacy in an SIV infected rhesus monkey model of HIV-infection.

Oral efficacy studies were conducted at New Iberia Research Center (NIRC), Lafayette, La. Following treatment with BAYTRIL® (5 mg/kg, IM, SID) for 5 days, 20 monkeys were inoculated intravenously with SIVmac251. After 3 days, venous blood was collected every 2-5 days (2× per week) for viral load testing and monitored to stable viremia (wherein 3 consecutive samples were within 3-fold of each other following acute viremia peak). Plasma SIV viral RNA levels were determined using a branched DNA technique at Siemens Diagnostics, Berkeley, Calif.

Following determination of stable viremia, SIV-infected monkeys were randomized by age, weight, and viral load (n=3 per group). A 2-arm adaptive design was employed in which results from Arm 1 informed the doses for Arm 2. In Arm 1, animals received two once-weekly doses of vehicle, 1.3 mg/kg EFdA, or 13 mg/kg EFdA administered via oral gavage. In Arm 2, animals received 3.9 mg/kg or 18.2 mg/kg EFdA once-weekly or 0.19 mg/kg EFdA once daily for two weeks. Blood (4 ml) was drawn for viral load determinations during the treatment period on days −2, 0 (dosing day), 1, 2, 3, 5, 7 (dosing day), 8, 9, 10, 12, and 14, and then two times per week for 3 weeks during the washout period. In addition, blood (1 ml) was drawn on days 0 (2 hrs post dose), 1 (24 hr post dose), 7 (2 hrs post dose), and 8 (24 hrs post dose) for EFdA pharmacokinetic assessment.

SIV RNA for genotyping was isolated from 140 µl plasma using the QIAamp Viral RNA Mini kit (Cat# 52904/52906). The reverse transcriptase region of SIVmac251 was reverse transcribed and amplified using SuperScript III RT/Platinum polymerase, primers S251RTF1 (GGCAAAAGGAT-TAAAGGGAC [2732-2751]) (SEQ ID NO:1) and S251RTR1 (TTTTACTTTGTCTTTGCCCC [4206-4225]) (SEQ ID NO: 2) and 8 µl template RNA in 20 µl reactions. A nested PCR reaction was carried out using 3.5 µl of the product from the first reaction with TaKaRa LA Taq and primers S251RTF2 (ACAATCATGACAGGGGACAC [2750-2769]) (SEQ ID NO: 3) and S251RTR2 (GCTTTC-CCTTCTTTTGACTG [4169-4188]) (SEQ ID NO: 4) in 50 µl reactions. After verifying size of ~1.5 kb by gel electrophoresis, PCR products were purified using ExoSAP-IT (Affymetrix; cat #78201) and adjusted to 15 ng/ml. PCR products (10µl) were mixed with 5 µl 5 µM sequencing primers S251RTS5 (CAGGGGACACTCCGATTAAC [2760-2779]) (SEQ ID NO: 5), s251RTS6 (AAGGTTCT-GCCTCAGGGATG [3266-3285]) (SEQ ID NO: 6), or S251RTS7 (CTCAGTCAGGAACAAGAAGG [3755-3774]) (SEQ ID NO: 7). DNA sequencing was carried out at Genewiz (115 Corporate Blvd, South Plainfield, NJ 07080).

The monkeys showed a high degree of variability in response among individuals. Those with high VLs exceeding 10 did not respond as well as those with low VLs and this contributed to a large standard deviation (FIG. 1). However, the groups were balanced with respect to VL and the averaged data shows a dose response curve with respect to VL reduction and return of VL upon cessation of dosing (washout). From 3.9 to 18.2 mg/kg QW, the VL drop appeared to be close to maximal and, even at 3.9 mg/kg, the VL suppression was maintained for 7 days from Day 7 to Day 14. One monkey in the vehicle group was euthanized around Day 19 due to poor clinical symptoms. There was a dose-dependent VL rebound during the wash-out period.

These experiments demonstrate that EFdA can control viremia with once-weekly oral administration as well as once-daily treatment.

EXAMPLE 2

Pharmacokinetics of EFdA following administration of oral doses in healthy humans.

The pharmacokinetics of EFdA were evaluated in Phase I single and multiple rising dose studies. In the single dose study, single oral doses of the oral suspension of EFdA from 5 to 400 mg were administered to three alternating panels of 8 healthy adult subjects. Within each panel, subjects were administered single doses of EFdA (n=6) or matching placebo (n=2) in a blinded fashion in up to 3 treatment periods. Panel A received 15 mg and 200 mg. Panel B received 30 mg, 400 mg, and 30 mg with food. Panel C received 100 mg and 5 mg. In the multiple rising dose study, multiple doses of EFdA oral capsules were administered to three panels of 8 healthy adult subjects. Within each panel, subjects were administered three once weekly doses of EFdA (n=6) or matching placebo (n=2) on Days 1, 8, and 15. Panel A received 10 mg. Panel B received 30 mg, and Panel C received 100 mg.

In the single dose study, EFdA-TP reached intracellular $C_{max}$ at a median $T_{max}$ of 6-24 hours and the concentrations in PBMCs declined with an apparent terminal half-life of ~120-210 hours. Intracellular EFdA pharmacokinetics were largely unaffected by a high-fat meal. EFdA was rapidly absorbed with a median Tmax of 0.5 hour. Plasma concentrations decreased in a bi-phasic manner with a rapid initial phase ($C_{max}$ reduced by approximately 10-fold within the first 6-12 hours) and a slow terminal phase with an apparent terminal half-life of ~50-60 hours. EFdA plasma exposure appeared to increase in an approximately dose-proportional manner between 5 and 400 mg.

Figure 2:
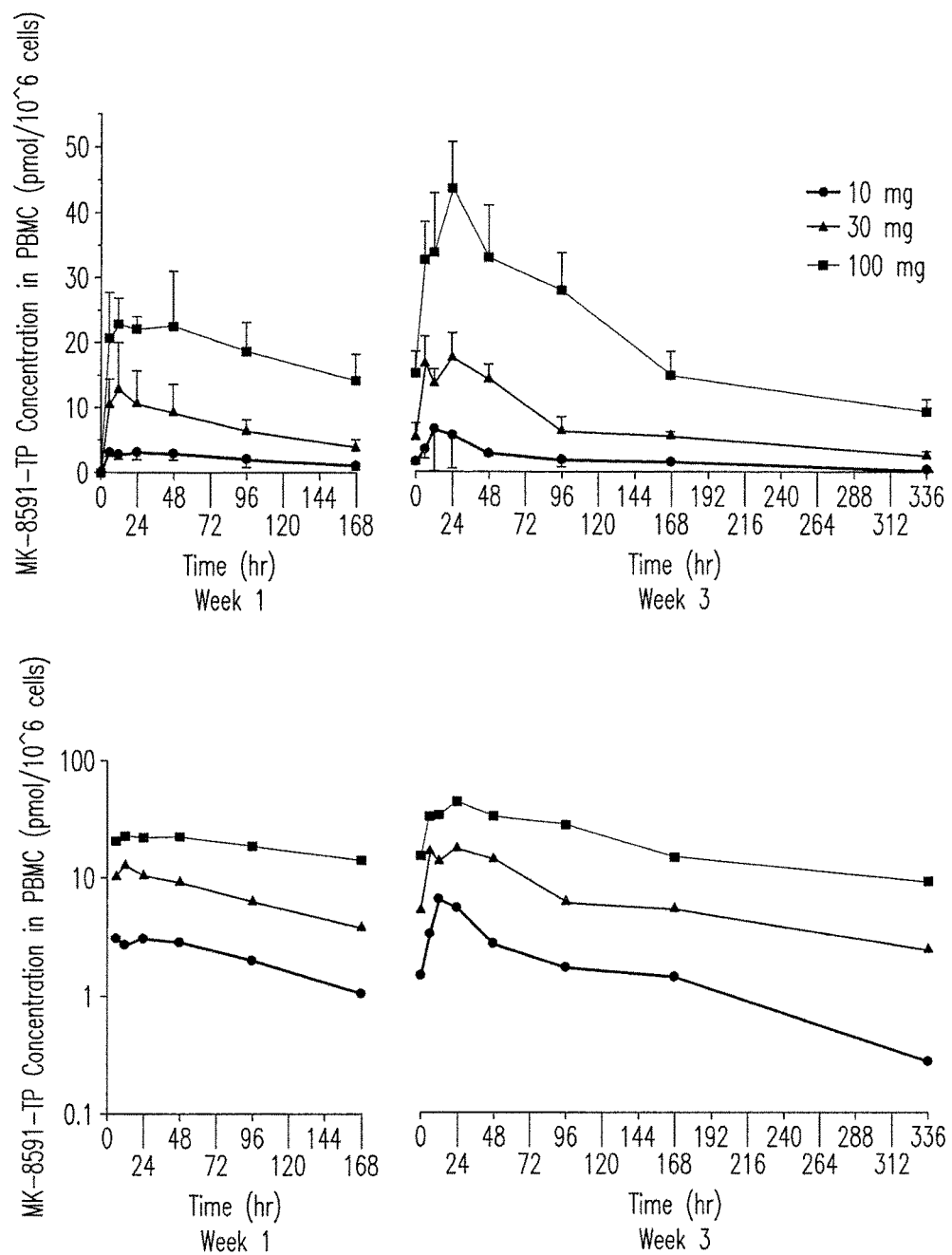
FIG. 2 is a graph of Mean PBMC Concentration versus Time Profiles for EFdA Triphosphate (TP) Following Administration of Once Weekly Oral Doses of EFdA for 3 Weeks to Healthy Fasted Subjects (linear scale) (lower, semi-log plot).
Figure 3:
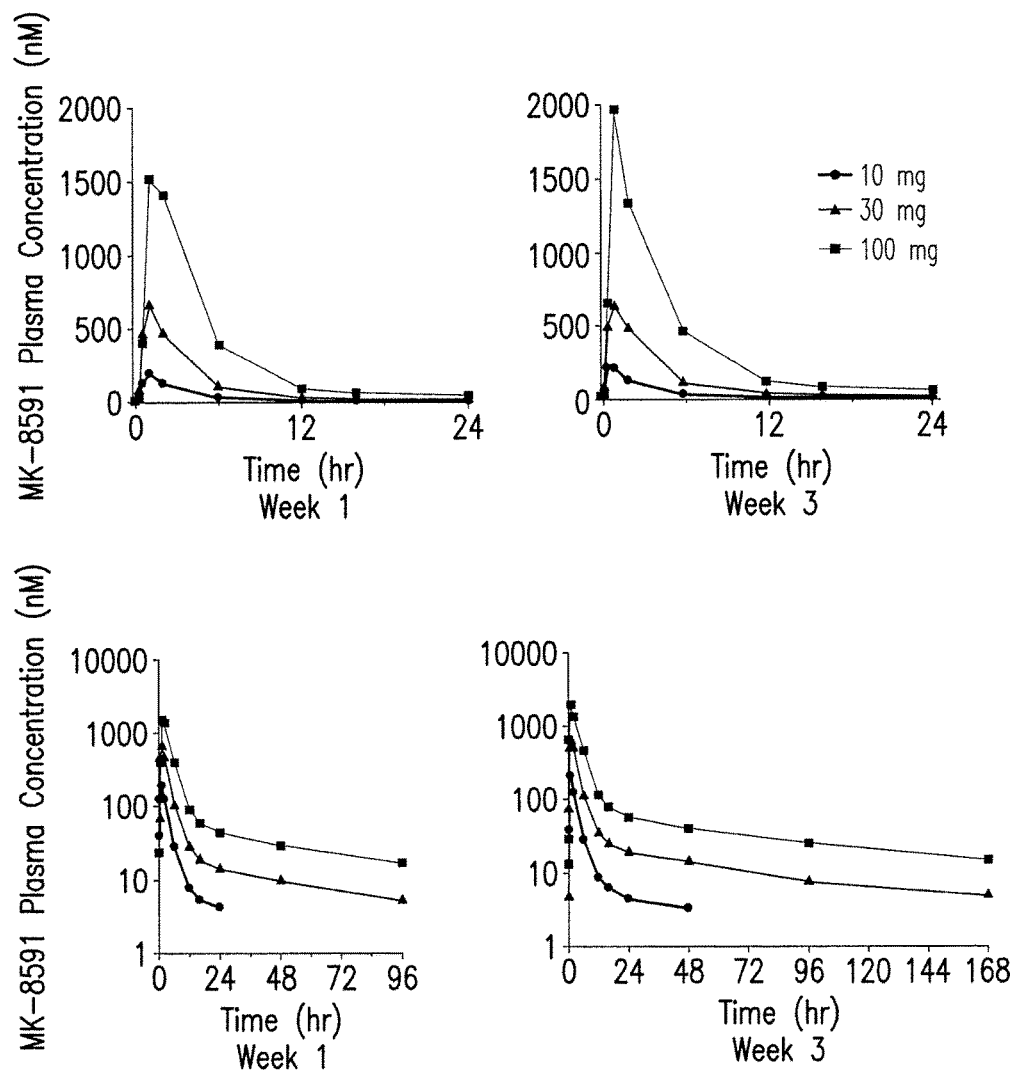
FIG. 3 is a graph of Mean EFdA Plasma Concentration versus Time Profiles Following Administration of Once Weekly Oral Doses of EFdA for 3 Weeks to Healthy Fasted Subjects (linear scale, first 24 hr post-dose) (lower, semi-log plot) (N=6, LOQ=3.41 nM).

Intracellular EFdA-triphosphate (TP) pharmacokinetics from the multiple dose study are shown in FIG. 2 and Table 1. Plasma EFdA pharmacokinetics from the multiple dose study are shown in FIG. 3 and Table 2. Results from the multiple dose study recapitulate results from the single dose study.

Following multiple doses of 30 mg and 100 mg there appeared to be a modest degree of accumulation of EFdA-TP $AUC_{0-168\ hr}$ and Cmax, while there was little to no accumulation of EFdA-TP $C_{168\ hr}$. There was little to no accumulation of EFdA in plasma, as anticipated from the relatively short half-life. All subjects had plasma concentrations below LLQ (3.41 nM) at 48 hr post-dose and later on week 1, and at 96 hr post-dose or later in week 3 at the 10 mg dose. The exposure of EFdA in plasma and EFdA-TP in PBMC appeared to increase in a generally dose-proportional manner.

TABLE 1

Summary Intracellular EFdA-TP in PBMCs Pharmacokinetic Parameter Values Following Administration of Once Weekly Oral Doses of EFdA for 3 Weeks to Healthy Fasted Subjects

| | | | Geometric Mean (% GCV) | | | | |
|---|---|---|---|---|---|---|---|
| Dose (mg) | N | Week | $AUC_{0-168\ hr}$ (hr * pmol/$10^6$ cells) | Cmax (pmol/$10^6$ cells) | $C_{168\ hr}$ (pmol/$10^6$ cells) | Tmax[†] (hr) | $t_{1/2}$ (hr) |
| 10 | 6 | 1 | 341 (21.2) | 3.78 (15.3) | 0.989 (40.4) | 48.00 (24.00, 96.00) | — |
| | | 3 | —[‡] | —[‡] | —[‡] | —[‡] | —[‡] |
| 30 | 6 | 1 | 1160 (41.5) | 13.2 (51.3) | 3.67 (35.8) | 9.00 (6.00, 24.00) | — |
| | | 3 | 1570 (12.3) | 19.6 (13.7) | 5.37 (10.7) | 15.00 (6.00, 24.00) | 150 (21.0) |
| | | AR[§] | 1.36 (0.97, 2.28) | 1.49 (0.87, 2.72) | 1.46 (1.10, 2.49) | — | — |
| 100 | 6 | 1 | 3020 (31.3) | 27.9 (21.2) | 13.5 (36.9) | 18.00 (6.00, 48.00) | — |
| | | 3 | 4580 (17.6) | 43.0 (16.7) | 14.3 (27.6) | 24.00 (12.00, 24.00) | 162 (14.6) |
| | | AR[§] | 1.52 (1.12, 2.44) | 1.54 (1.35, 2.09) | 1.06 (0.74, 1.48) | — | — |

PBMC: Peripheral Blood Mononuclear Cells
[†]Median (Min, Max)
[‡]30% of PBMC samples of week 3 were lost during shipping due to mishandling. Therefore, the PK parameter values could not be determined.
[§]Geometric Mean Accumulation Ratio of Week 3/Week 1(Min, Max)

TABLE 2

Summary EFdA Plasma Pharmacokinetic Parameter Values Following Administration of Once Weekly Oral Doses of EFdA for 3 Weeks to Healthy Fasted Subjects

| | | | Geometric Mean (% GCV) | | | |
|---|---|---|---|---|---|---|
| Dose (mg) | N | Week | $AUC_{0-168\ hr}$‡ (μM * hr) | Cmax (nM) | Tmax† (hr) | $t_{1/2}$ (hr) |
| 10 | 6 | 1 | — | 193 (40.8) | 1.00 (0.50, 2.00) | — |
| | | 3 | —& | 241 (48.9) | 1.00 (0.50, 1.00) | —& |
| | | AR§ | — | 1.25 (0.70, 1.66) | — | — |
| 30 | 6 | 1 | — | 647 (25.3) | 1.00 (0.50, 1.00) | — |
| | | 3 | 3.97 (18.5) | 637 (31.0) | 1.00 (0.50, 1.00) | 74.1 (14.1) |
| | | AR§ | — | 0.98 (0.73, 1.44) | — | — |
| 100 | 6 | 1 | — | 1470 (65.1) | 2.00 (1.00-6.00) | — |
| | | 3 | 12.0 (14.8) | 1850 (62.2) | 1.00 (1.00-6.00) | 87.1 (9.55) |
| | | AR§ | — | 1.26 (0.26, 3.59) | — | — |

‡$AUC_{0-168hr}$ could not be determined for week 1 as plasma samples were collected up to 96 hrs for Week 1
†Median (Min, Max)
§Geometric Mean Accumulation Ratio of Week 3/Week 1(Min, Max)
&Values could not be determined due to insufficient data in the terminal phase.

EXAMPLE 3

The single dose monotherapy efficacy of EFDA is currently being evaluated in HIV-1 patients naïve to anti-retroviral treatment. In this study a single 10 mg dose of EFDA was associated with a rapid and robust reduction in VL. At 168 hours post-dose, a mean (95% CI) placebo adjusted VL reduction of 1.67 log 10 (1.47, 1.87) was observed. Mean VL continued to decline through Day 10 with a mean reduction of 1.78 log 10 (1.59, −1.98) and no evidence of recrudescence. The 10-mg dose was generally well tolerated with a limited number of mild/moderate adverse experiences reported. EFDA plasma and EFDA-TP PBMC PK were similar to previously reported data in healthy subjects. A summary of the placebo corrected change from baseline in viral load for a 10 mg dose is provided in Table 3 below.

TABLE 3

Placebo Corrected Change from Baseline in Viral Load for a 10 mg Dose of EFDA

| Treatment | N | Min | Median | Max | SD† | LS mean‡ (95% CI§) |
|---|---|---|---|---|---|---|
| PBO | 20 | −0.52 | −0.04 | 0.42 | 0.25 | −0.03 (−0.13, 0.08) |
| Panel A: EFDA | 6 | −1.97 | −1.63 | −1.31 | 0.24 | −1.67 (−1.87, −1.47) |

| | Posterior mean | PP‖ |
|---|---|---|
| EFDA adjusted by PBO | −1.64 | >99.9% |

†SD = standard deviation;
‡LS = least squares.
§CI = confidence interval.
The PBO data were pooled from historical placebo data from recent monotherapy studies in HIV patients and fitted with a longitudinal data analysis model containing fixed effects for study and time, and a random effect for subject. The EFdA data were fitted with a longitudinal data analysis (LDA) model containing fixed effects for treatment, time and treatment by time interaction, and a random effect for subject.
‖PP = Posterior Probability of true mean difference in the plasma HIV-1 RNA reduction from baseline between EFDA and placebo at least 0.5 log10 copies/mL

What is claimed is:

1. A method for the prophylaxis of HIV infection in a subject which comprises orally administering to the subject an effective amount of a compound of structural formula:

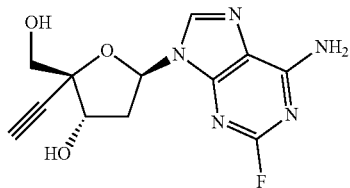 [SMILES: C#C[C@]1(CO)O[C@@H](n2cnc3c(N)nc(F)nc32)C[C@@H]1O]

or a pharmaceutically acceptable salt thereof, wherein the dosing regimen is once-weekly, bi-weekly, twice monthly or once-monthly.

2. The method of claim 1 wherein the subject is human.

3. The method of claim 2 wherein the dosing regimen is once-weekly.

4. The method of claim 3 wherein the dosage amount is from 1 mg to 50 mg at each administration.

5. The method of claim 2 wherein the dosing regimen is bi-weekly or twice monthly.

6. The method of claim 5 wherein the dosage amount is from 2 mg to 100 mg at each administration.

7. The method of claim 2 wherein the dosing regimen is once-monthly.

8. The method of claim 7 wherein the dosage amount is from 4 mg to 200 mg at each administration.

9. A method for the prophylaxis of HIV infection in a subject which comprises orally administering to the subject an effective amount of a compound of structural formula:

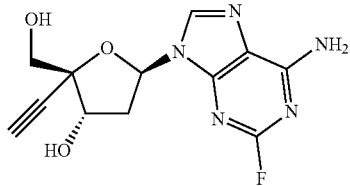 [SMILES: C#C[C@]1(CO)O[C@@H](n2cnc3c(N)nc(F)nc32)C[C@@H]1O]

wherein the dosing regimen is once-weekly, bi-weekly, twice monthly or once-monthly.

10. The method of claim 9 wherein the subject is human.

11. The method of claim 10 wherein the dosing regimen is once-weekly.

12. The method of claim 11 wherein the dosage amount is from 1 mg to 50 mg at each administration.

13. The method of claim 10 wherein the dosing regimen is bi-weekly or twice monthly.

14. The method of claim 13 wherein the dosage amount is from 2 mg to 100 mg at each administration.

15. The method of claim 10 wherein the dosing regimen is once-monthly.

16. The method of claim 15 wherein the dosage amount is from 4 mg to 200 mg at each administration.

17. The method of claim 1 for the prophylaxis of HIV-1 infection.

18. The method of claim 2 for the prophylaxis of HIV-1 infection.

19. The method of claim 3 for the prophylaxis of HIV-1 infection.

20. The method of claim 4 for the prophylaxis of HIV-1 infection.

21. The method of claim 5 for the prophylaxis of HIV-1 infection.

22. The method of claim 6 for the prophylaxis of HIV-1 infection.

23. The method of claim 7 for the prophylaxis of HIV-1 infection.

24. The method of claim 8 for the prophylaxis of HIV-1 infection.

25. The method of claim 9 for the prophylaxis of HIV-1 infection.

26. The method of claim 10 for the prophylaxis of HIV-1 infection.

27. The method of claim 11 for the prophylaxis of HIV-1 infection.

28. The method of claim 12 for the prophylaxis of HIV-1 infection.

29. The method of claim 13 for the prophylaxis of HIV-1 infection.

30. The method of claim 14 for the prophylaxis of HIV-1 infection.

31. The method of claim 15 for the prophylaxis of HIV-1 infection.

32. The method of claim 16 for the prophylaxis of HIV-1 infection.

* * * * *

SEQUENCE LISTING

<160> NUMBER OF SEQ ID NOS: 7

<210> SEQ ID NO 1
<211> LENGTH: 20
<212> TYPE: DNA
<213> ORGANISM: Artificial Sequence
<220> FEATURE:
<223> OTHER INFORMATION: PRIMERS

<400> SEQUENCE: 1
ggcaaaagga ttaaagggac                                                     20

<210> SEQ ID NO 2
<211> LENGTH: 20
<212> TYPE: DNA
<213> ORGANISM: Artificial Sequence
<220> FEATURE:
<223> OTHER INFORMATION: PRIMERS

<400> SEQUENCE: 2
ttttactttg tctttgcccc                                                     20

<210> SEQ ID NO 3
<211> LENGTH: 20
<212> TYPE: DNA
<213> ORGANISM: Artificial Sequence
<220> FEATURE:
<223> OTHER INFORMATION: PRIMERS

<400> SEQUENCE: 3
acaatcatga cagggacac                                                      20

<210> SEQ ID NO 4
<211> LENGTH: 20
<212> TYPE: DNA
<213> ORGANISM: Artificial Sequence
<220> FEATURE:
<223> OTHER INFORMATION: PRIMERS

<400> SEQUENCE: 4 gctttcccctt cttttgactg                                                    20

<210> SEQ ID NO 5
<211> LENGTH: 20
<212> TYPE: DNA
<213> ORGANISM: Artificial Sequence
<220> FEATURE:
<223> OTHER INFORMATION: PRIMERS

<400> SEQUENCE: 5 cagggggacac tccgattaac                                                    20

<210> SEQ ID NO 6
<211> LENGTH: 20
<212> TYPE: DNA
<213> ORGANISM: Artificial Sequence
<220> FEATURE:
<223> OTHER INFORMATION: PRIMERS

<400> SEQUENCE: 6
aaggttctgc ctcagggatg                                                     20

<210> SEQ ID NO 7
<211> LENGTH: 20
<212> TYPE: DNA
<213> ORGANISM: Artificial Sequence

```
<220> FEATURE:
<223> OTHER INFORMATION: PRIMERS

<400> SEQUENCE: 7
ctcagtcagg aacaagaagg                                                    20
```